United States Patent
Bäckström et al.

(10) Patent No.: US 6,610,653 B1
(45) Date of Patent: *Aug. 26, 2003

(54) THERAPEUTIC PREPARATION FOR INHALATION

(75) Inventors: Kjell Göran Erik Bäckström, Lund (SE); Carl Magnus Olof Dahlbäck, Lund (SE); Peter Edman, Bjärred (SE); Ann Charlotte Birgit Johansson, Lund (SE)

(73) Assignee: AstraZeneca AB, Södertälje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 09/665,585

(22) Filed: Sep. 18, 2000

Related U.S. Application Data (60) Division of application No. 09/072,717, filed on May 5, 1998, now Pat. No. 6,165,976, which is a continuation of application No. 08/583,205, filed on Jan. 4, 1996, now Pat. No. 5,747,445, which is a continuation-in-part of application No. 08/265,372, filed on Jun. 23, 1994, now Pat. No. 5,518,998.

(51) Int. Cl.[7] .................... A61K 38/28; C07K 14/62
(52) U.S. Cl. ................. 514/3; 514/4; 514/975; 530/303
(58) Field of Search ............... 514/3, 4, 975; 424/499

(56) References Cited

U.S. PATENT DOCUMENTS

| | | | |
|---|---|---|---|
| 2,992,645 A | 7/1961 | Fowler | |
| 3,014,844 A | 12/1961 | Thiel et al. | 167/82 |
| 3,911,138 A | 10/1975 | Clark, Jr. | |
| 4,524,769 A | 6/1985 | Wetterlin | 128/203.15 |
| 4,534,345 A | 8/1985 | Wetterlin | 128/203.15 |
| 4,537,772 A | 8/1985 | Alexander et al. | 514/9 |
| 4,548,922 A | 10/1985 | Carey et al. | 514/4 |
| 4,613,500 A | 9/1986 | Suzuki et al. | 424/85.4 |
| 4,668,218 A | 5/1987 | Virtanen | 604/58 |
| 4,690,952 A | 9/1987 | Kagatani et al. | 514/11 |
| 4,731,360 A | 3/1988 | Alexander et al. | 514/201 |

(List continued on next page.)

FOREIGN PATENT DOCUMENTS

| | | |
|---|---|---|
| DE | 261 096 A1 | 10/1988 |
| EP | 0 023 359 | 7/1980 |
| EP | 0 055 041 | 12/1981 |

(List continued on next page.)

OTHER PUBLICATIONS

Lecluyse et al. J. Pharmacol. Exp. Ther. (1993), 265(2), 955–62.*
Goni et al. FEBS Lett. (1996), 390(1), 1–5.*
Almer et al., "Insulin Inhalation—At Last a Breakthrough," Diabetes Res. And Clin. Pract., 5:s163, 1988. (1988).
Byron et al., "Drug Delivery via the Respiratory . . . ," Journal of Aerosol Medicine, 7:49–75, 1994.

(List continued on next page.)

*Primary Examiner*—Michael Borin
(74) *Attorney, Agent, or Firm*—Fish & Richardson P.C.

(57) ABSTRACT

A therapeutic preparation for inhalation which comprises insulin and a substance which enhances the absorption of insulin in the lower respiratory tract, is provided in the form of a powder preparation suitable for inhalation.

34 Claims, 6 Drawing Sheets

U.S. PATENT DOCUMENTS

| | | | |
|---|---|---|---|
| 4,746,508 A | 5/1988 | Carey et al. | 424/88 |
| 4,788,221 A | 11/1988 | Kagatani et al. | 514/12 |
| 4,847,298 A | 7/1989 | Alexander et al. | 514/565 |
| 4,895,719 A | 1/1990 | Radhakrishnan et al. | 424/45 |
| 4,900,730 A | 2/1990 | Miyauchi | 514/12 |
| 4,907,583 A | 3/1990 | Wetterlin et al. | 128/203.15 |
| 4,914,084 A | 4/1990 | Ecanow | |
| 4,920,061 A | 4/1990 | Poynton et al. | |
| 4,926,852 A | 5/1990 | Zoltan et al. | 128/200.23 |
| 4,959,358 A | 9/1990 | Carey et al. | 514/171 |
| 4,963,367 A | 10/1990 | Ecanow | 424/485 |
| 4,994,439 A | 2/1991 | Longenecker et al. | 514/3 |
| 5,006,343 A | 4/1991 | Benson et al. | |
| 5,011,678 A | 4/1991 | Wang et al. | 424/45 |
| 5,118,494 A | 6/1992 | Schultz et al. | 424/45 |
| 5,122,127 A | 6/1992 | Stanley | 604/809.1 |
| 5,122,376 A | 6/1992 | Aliverti et al. | 424/408 |
| 5,179,079 A | 1/1993 | Hansen et al. | 514/4 |
| 5,192,548 A | 3/1993 | Velasquez et al. | 424/443 |
| 5,200,393 A | 4/1993 | Weiner | 514/3 |
| 5,202,129 A | 4/1993 | Samejima et al. | 424/489 |
| 5,254,330 A | 10/1993 | Ganderton et al. | 424/46 |
| 5,260,306 A | 11/1993 | Boardman et al. | 514/291 |
| 5,284,656 A | 2/1994 | Platz et al. | 424/435 |
| 5,288,498 A | 2/1994 | Stanley et al. | 424/440 |
| 5,320,094 A | 6/1994 | Laube et al. | 128/203.12 |
| 5,341,800 A | 8/1994 | Clark et al. | 128/203.15 |
| 5,348,730 A | 9/1994 | Greenleaf et al. | |
| 5,349,947 A | 9/1994 | Newhouse et al. | 128/203.21 |
| 5,352,461 A | 10/1994 | Feldstein et al. | 424/493 |
| 5,354,562 A | 10/1994 | Platz et al. | 424/489 |
| 5,364,838 A | 11/1994 | Rubsamen | 514/3 |
| 5,376,386 A | 12/1994 | Ganderton et al. | 424/449 |
| 5,384,133 A | 1/1995 | Boyes et al. | 424/501 |
| 5,419,315 A | 5/1995 | Rubsamen | 128/200.14 |
| 5,437,271 A | 8/1995 | Hodson et al. | 128/203.15 |
| 5,451,569 A | 9/1995 | Wong et al. | 514/3 |
| 5,458,135 A | 10/1995 | Patton et al. | 128/200.14 |
| 5,474,759 A | 12/1995 | Fassberg et al. | |
| 5,482,032 A | 1/1996 | Smith et al. | 128/203.15 |
| 5,482,706 A | 1/1996 | Igari et al. | 424/85.7 |
| 5,506,203 A | 4/1996 | Bäckström et al. | 514/4 |
| 5,514,670 A | 5/1996 | Friedman et al. | 514/2 |
| 5,518,998 A | 5/1996 | Backstrom et al. | 514/3 |
| 5,607,915 A | 3/1997 | Patton | 514/12 |
| 5,661,130 A | 8/1997 | Meezan et al. | 514/25 |
| 5,707,644 A | 1/1998 | Illum | 424/434 |
| 5,730,969 A | 3/1998 | Hora et al. | 424/85 |
| 5,814,607 A | 9/1998 | Patton | 514/12 |
| 5,997,848 A | 12/1999 | Patton et al. | 424/46 |
| 6,051,256 A | 4/2000 | Platz et al. | 424/489 |

FOREIGN PATENT DOCUMENTS

| | | | |
|---|---|---|---|
| EP | 0 128 831 | 12/1984 | |
| EP | 0 200 383 | 4/1986 | |
| EP | 0 225 189 | 6/1987 | |
| EP | 0 272 097 | 6/1988 | |
| EP | 0 360 340 | 3/1990 | |
| EP | 0 455 463 | 11/1991 | |
| GB | 837465 | 6/1960 | |
| GB | 1242211 | 8/1971 | |
| GB | 1520247 | 8/1978 | |
| GB | 1 527 605 | 10/1978 | |
| GB | 1569611 | 6/1980 | |
| JP | 1117825 | 2/1987 | |
| JP | 632932 | 7/1988 | |
| JP | 4041421 | 6/1990 | |
| JP | Hei 4-41421 | 2/1992 | |
| JP | Hei 4-149126 | 5/1992 | |
| SE | 8007820-7 | 9/1981 | |
| WO | WO 88/09163 | 12/1988 | |
| WO | WO 90/07333 | 4/1990 | |
| WO | WO 91/16038 | 10/1991 | |
| WO | WO 91/16882 | 11/1991 | A61K/9/14 |
| WO | WO 92/04069 | 3/1992 | |
| WO | WO 92/06704 | 4/1992 | |
| WO | WO 92/08446 | 5/1992 | |
| WO | WO 94/07514 | 4/1994 | |
| WO | WO 97/10850 | 3/1997 | |

OTHER PUBLICATIONS

Cutie et al., "The Role of Dispersing Agents in Inhalation and Intranasal Aerosol Suspensions," Aerosol. Age 30:52–54, 1985.

Dahlbäck et al., "Regional Administration of Drugs to the Rabbit Respiratory Tract, Effects on Absorption," J. Aerosol Medicine 1:222–223, 1988.

Elliot et al., "Parenteral absorption of insulin . . . ," Aust. Paediatr. J., 23:293–297, 1987.

Jaegfeldt, H. et al., "Particle size distribution from different modifications of Turbuhaler®," Proceedings of an international workshop on a new inhaler, May 21–22, 1987 (London) pp. 90–99.

Lee et al., "Mucosal Penetration Enhancers for Facilitaion of Peptide and Protein Drug Absorption," Critical Rev. Therapeut. Drug Carrier Systems 8:91–192, 1991.

Li, Yuping et al., "Effect of a Conjugated Bile Salt on the Pulmonary Absorption of Insulin in Rats," Eur. J. Biopharm., vol. 39, pp. 216–221, 1993.

Liu et al., "Pulmonary Delivery of Free . . . ," Pharmaceutical Research, 10:228–232, 1993.

Moses et al., "Insulin Administered Intranasally as an Insulin–Bile Salt Aerosol," Diabetes 32:1040–47, 1983.

Nagano et al., "New Method of Insulin . . . " Jikeikai Med. J., 32:503–506, 1985.

Okumura et al., "Intratracheal delivery of insulin: Absorption from solution and aerosol by rat lung," International Journal of Pharmaceutics, vol. 88, pp. 63–73, 1992.

Ruin, Sydsvenska (Dagbladet), Monday, Jun. 12, 1989, "Diabetics May Not Need Their Insulin Shots".

Sakr., "A new approach for insulin . . . ," International Journal of Pharmaceutics, 86:1–7, 1992.

Salzman et al., "Intranasal Aerosolized . . . ," The New England Journal of Medicine, 312:1078–1084, 1985.

Timsina et al., "Drug Delivery to the Respiratory Tract Using Dry Powder Inhalers," Int. J. Pharmaceutics 101:1–13, 1994.

Wearley, "Recent Progress in Protein and Peptide Delivery by Noninvasive Routes," Critical Rev. Therapeut. Drug Carrier Systems, 8:331–394, 1991.

Wetterlin, Kjell, "Turbuhaler: A New Powder Inhaler for Administration of Drugs to the Airways," Pharmaceutical Research, vol. 5, pp. 506–508, 1988.

Yamamoto et al., "Absorption Enhancement of Intrapulmonary Administered Insulin by Various Absorption . . . ," J. Pharm. Pharmacol., vol. 46, pp. 14–18, 1994.

Yoshida et al., "Absorption of Insulin Delivered to Rabbit Trachea Using Aerosol Dosage Form," J. Pharm. Sci. 68:670–671, 1979.

Bjork et al., "Characterization of degradable starch . . . ", Int. J. Pharmaceutics, 62 (1990) 187–192.

Jones, "Pulmonary Absorption of Insulin", (1998) Ph.D. Thesis, Welsh School of Pharmacy, University of Wales, United Kingdom.

Lee et al., "Development of an Aerosol Dosage Form Containing Insulin", J. Pharmaceutical Sciences, vol. 65, No. 4, (1976) 567–574.

Newman, "Chapter 9: Therapeutic aerosols", In: Aerosols and the Lung: Clinical and Experimental Aspects, (1984) Butterworth & Co., United Kingdom.

Allenby et al., The Absorption of Insulin Across the Respiratory Tract of the Guinea–Pig (U), The Aerosol Society, Fourth Annual Conference 1990, pp. 129–134.

Aungst and Rogers, Comparison of the Effects of Various Transmucosal Absorption Promoters on Buccal Insulin Delivery, Int. J. Pharm. (Netherlands), 1989, 53/3, 227–235.

Björk, Starch Microspheres as a Nasal Delivery System for Drugs, Comprehensive Summaries of Uppsala Dissertations from the Faculty of Pharmacy 103, 1993.

Björk and Edman, Degradable Starch Microspheres as a Nasal Delivery System for Insulin, Int. J. Pharm. 47:233–238, 1988.

Brange et al., Monomeric Insulins and Their Experimental and Clinical Implications, Diabetes Care 13:923–954, 1990.

Edman and Björk, Routes of Delivery: Case Studies, Advanced Drug Delivery Reviews 8:165–177, 1992.

Igawa et al., Effect of Absorption Promoters in Intranasal Administration of Human Fibroblast Interferon as a Powder Dosage Form in Rabbits, Chem. Pharm. Bull. 37:418–421, 1989.

Komada et al., Intratracheal Delivery of Peptide and Protein Agents: Absorption from Solution and Dry Powder by Rat Lung, J. Pharm. Sci. 83:863–867, 1994.

Lasker, The Diabetes Control and Complications Trial, N. Engl. J. Med. 329:1035–1036, 1993.

Laube et al., Preliminary Study of the Efficacy of Insulin Aerosol Delivered by Oral Inhalation in Diabetic Patients, JAMA 269:2106–2109, 1993.

Lee et al., Intranasal Bioavailability of Insulin Powder Formulations: Effect of Permeation Enhancer–to–Protein Ratio, J. Pharm. Sci. 80:725–729, 1991.

Mishima et al., Studies on the Promoting Effects of Medium Chain Fatty Acid Salts on the Nasal Absorption of Insulin in Rats, J. Pharma –Dyn. 10:624–631, 1987.

Morita et al., Effects of Various Absorption Promoters on Pulmonary Absorption of Drugs with Different Molecular Weights, Biol. Pharm. Bull. 16:269–262, 1993.

Nagai et al., Powder Dosage Form of Insulin for Nasal Administration, J. Controlled Release 1:15–22, 1984.

"Diabetes Mellitus", Ch. VI in Scientific American Medicine, Scientific American, Inc., Apr. 1993.

The Diabetes Control and Complications Trial Research Group, The Effect of Intensive Treatment of Diabetes on the Development . . . Complications in Insulin–Dependent Diabetes Mellitus, N. Engl. J. Med. 329:977–86, 1993.

Pontiroli et al., Nasal Administration of Glucagon and Human Calcitonin to Healthy Subjects: a Comparison of Powders and Spray Solutions and of Different Enhancing Agents, Eur. J. Clin. Pharmacol. 37:427–430, 1989.

Schipper et al., Nasal Insulin Delivery with Dimethyl–β–Cyclodextrin as an Absorption Enhancer in Rabbits: Powder More Effective than Liquid Formulations, Pharmaceutical Research 10:682–686, 1993.

Selam and Charles, Devices for Insulin Administration, Diabetes Care 13:955–979, 1990.

Touitou and Rubenstein, Targeted Enteral Delivery of Insulin to Rats, Int. J. Pharm. (Amst.), 30(2–3), 1986, 95–100.

Wigley et al., Insulin Across respiratory Mucosae by Aerosol Delivery, Diabetes 20:552–556, 1971.

Zinman, Medical Intelligence—The Physiologic Replacement of Insulin, N. Engl. J. Med. 321:363–370, 1989.

Olanoff et al., "Method to Enhance Intranasal Peptide Delivery," in "Controlled–Release Technology Pharmaceutical Applications," Lee et al., American Chemical Societ, 301–309, 1987.

Chien et al., "Intranasal Drug Delivery For Systemic Medications", CRC Critical Reviews in Therapeutic Drug Carrier Systems 4:67–194, 1987.

Eppstein et al., "Alternative Delivery Systems for Peptides and Proteins As Drugs", CRC Critical Reviews in Therapeutic Drug Carrier Systems 5:99–139, 1988.

O'Hagan et al., "Absorption of Peptides and Proteins from the Respiratory Tract and the Potential for Development of Locally Administered Vaccine", Critical Reviews in Therapeutic Drug Carrier Sys 7:35–97, 1990.

Dieter Köhler,—Aerosols for Systemic Treatment, Lung (1990) Suppl:677–684.

Maarten A.J.M Jacobs, "The Pharmacodynamics and Activity of Intranasally Administered Insulin in Healthy Male Volunteers", DIABETES, vol., 42, Nov. 1993, pp. 1649–1655.

Bruce J. Aungst, et al, "Comparison of Nasal, Rectal, Buccal, Sublingual and Intramuscular Insulin Efficacy and the Effects of a Bile Salt Absorption Promoter", The Journal of Pharmacology and Experimental Therapeutics, vol. 244, No. 1, 1987.

Köhler et al., "Pulmonary Administration . . . Type I Diabestes," Abstract #298, Diabetes 33(Suppl.):75A, 1984.

Jennifer L. Hoover et al, "Peptides are Better Absorbed from the Lung than the Gut in the Rat", Pharmaceutical Research, vol. 9, No. 8, 1992, pp. 1103–1106.

Paul Colthorpe et al, "The Pharmacokinetics of Pulmonary–Delivered Insulin: A Comparison of Intratracheal . . . ", Pharmaceutical Research, vol. 9, No. 6, 1992; pp.764–769.

D. Köhler et al, "Nicht radioaktives Verfahren zur Messung der Lungenpermeabilitat: Inhalation von Insulin", Atenw–Lungenkrkh, Jahrgang 13, Nr. Jun. 1987; 230–232.

Yie W. Chien et al, "Potential Developments in Systemic Delivery of Insulin", Druge Development and Industrial Pharmacy, 15(10), 1989, 1601–1634.

John s. Patton et al, "(D) Routes of Delivery: Case Studies", Advanced Drug Delivery Reviews, 8 (1992) pp. 179–196.

* cited by examiner

Transport of mannitol across Caco-2 cell monolayer in presence of Na-caprate (10-16mM)

A. Na-caprate
B. Na-caprate/insulin (1:3 w/w)

THERAPEUTIC PREPARATION FOR INHALATION

This application is a divisional of U.S. Ser. No. 09/072,717, filed May 5, 1998 now U.S. Pat. No. 6,165,976, now allowed, which is a continuation of 08/583,205, filed Jan. 4, 1996, now U.S. Pat. No. 5,747,445, which is a continuation-in-part of U.S. Ser. No. 08/265,372, filed Jun. 23, 1994 now U.S. Pat. No. 5,518,998. The invention relates to a therapeutic preparation of insulin suitable for inhalation.

BACKGROUND OF THE INVENTION

Insulin plays a central role in the regulation of carbohydrate, fat, and protein metabolism in the body. Diabetes mellitus (commonly referred to simply as diabetes) is a disease characterized by disregulation of metabolism, particularly glucose metabolism. In normal individuals, a rise in blood glucose levels (such as that which occurs immediately following eating) triggers the islet beta cells of the pancreas to secrete insulin, a peptide hormone, into the bloodstream. The insulin binds to insulin receptors located on a number of cell types, notably muscle cells, and thereby signals the cells to increase the rate of glucose uptake into the cells. As the blood glucose returns to normal pre-prandial levels, the amount of insulin in the blood also drops. In the absence of insulin, blood glucose levels would rise to dangerously high levels (a condition termed hyperglycemia), possibly resulting in death. Too much insulin causes abnormally low blood glucose levels (hypoglycemia), which is also dangerous and possibly fatal. In a normal individual, built-in feedback loops regulating the secretion of insulin and its clearance from the systemic circulation prevent both hyperglycemic and hypoglycemic conditions from occurring.

Diabetes mellitus is a disease affecting about 3% of the population of Sweden of these 3%, approximately 20% suffer from Type I diabetes, and the remainder from Type II diabetes.

Type I diabetes, or insulin-dependent diabetes mellitus (IDDM), usually begins in childhood. It is characterized by atrophy of the pancreatic beta cells, resulting in a decrease or cessation of insulin production, and leaving the patient dependent on exogenous insulin for survival.

The more common Type II diabetes, or non-insulin-dependent diabetes mellitus (NIDDM), generally occurs in patients older than 40 years. These patients may, at least initially, have normal or even high levels of insulin in their blood, but exhibit an abnormally low rate of cellular uptake of glucose in response to insulin. Although Type II diabetes often can be treated by controlling the patient's diet, administration of exogenous insulin to supplement that secreted by the patient's beta cells may also prove necessary.

Insulin cannot be orally administered in effective doses, since it is rapidly degraded by enzymes in the gastrointestinal tract and low pH in the stomach before it can reach the bloodstream. The standard method of administration is by subcutaneous injection of an isotonic solution of insulin, usually by the patient him/herself. The necessity for injection causes a great deal of inconvenience and discomfort to many sufferers, and local reactions can occur at the injection site. In addition there is an abnormal, non-physiological, plasma concentration profile for injected insulin. This abnormal plasma concentration profile is undesirable and increases the risk of side effects related to the long term treatment of diabetes.

Because of these disadvantages, there is a need for insulin in a form which is administrable other than by injection. In attempts to produce such different forms of insulin, various proposals have been made. For example, products for nasal, rectal and buccal administration have been suggested, with much effort being concentrated on products for nasal administration. Pulmonary delivery of systemically active drugs has gained increasing interest over the last years, and some investigations have included the pulmonary delivery of insulin. Most of these are concerned with solutions or suspensions for pulmonary delivery, for example by nebulisers and pressurised metered dose inhalers, and all have met with limited success.

SUMMARY OF THE INVENTION

We have now found that insulin can be included in a dry powder preparation for inhalation also including a substance which enhances the absorption of insulin in the lung, from which preparation the insulin may be absorbed in a therapeutically acceptable rate and amount. By "enhances absorption" is meant that the amount of insulin absorbed into the systemic circulation in the presence of the enhancer is higher than the amount absorbed in the absence of enhancer.

According to this invention, there is provided a therapeutic preparation comprising active compounds (A) insulin, and (B) a substance which enhances the absorption of insulin in the lower respiratory tract, which preparation is in the form of a dry powder suitable for inhalation in which at least 50% of the total mass of active compounds consists of (a) primary particles having a diameter of less than about 10 microns, for example between 0.01 and microns and preferably between 1 and 6 microns, or (b) agglomerates of said particles.

The therapeutic preparation of the present invention may contain only the said active compounds or it may contain other substances, such as a pharmaceutically acceptable carrier. This carrier may largely consist of particles having a diameter of less than about 10 microns so that at least 50% of the resultant powder as a whole consists of optionally agglomerated primary particles having a diameter 10 of less than about 10 microns; alternatively the carrier may largely consist of much bigger particles ("coarse particles"), so that an "ordered mixture" may be formed between the active compounds and the carrier. In an ordered mixture, alternatively known as an interactive or adhesive mixture, fine drug particles (in this invention, the active compounds) are fairly evenly distributed over the surface of coarse excipient particles (in this invention, the pharmaceutically acceptable carrier). Preferably, the active compounds are not in the form of agglomerates prior to formation of the ordered mixture. The coarse particles may have a diameter of over 20 microns, such as over 60 microns. Above these lower limits, the diameter of the coarse particles is not of critical importance, so various coarse particle sizes may be used, if desired, according to the practical requirements of the particular formulation. There is no requirement for the coarse particles in the ordered mixture to be of the same size, but the coarse particles may advantageously be of similar size within the ordered mixture. Preferably, the coarse particles have a diameter of 60–800 microns.

In a particular embodiment therefore this invention provides a therapeutic preparation of insulin and a substance which enhances the absorption of insulin in the lower respiratory tract, which preparation is in the form of a dry powder preparation suitable for inhalation of which at least-50% by mass consists of (a) particles having a diameter of less than about 10 microns or (b) agglomerates of said particles; in a further particular embodiment, the invention provides a therapeutic preparation comprising insulin, a substance which enhances the absorption of insulin in the lower respiratory tract, and a pharmaceutically acceptable carrier, which preparation is in the form of a dry powder suitable for inhalation of which at least 50% by mass consists of (a) particles having a diameter of less than about 10 microns, or (b) agglomerates of said particles; and in a still further particular embodiment this invention provides a therapeutic preparation comprising active compounds (A) insulin and (B) a substance which enhances the absorption of insulin in the lower respiratory tract, wherein at least 50% of the total mass of active compounds (A) and (B) consists of particles having a diameter of less than about 10 microns, and a pharmaceutically acceptable carrier, which preparation is in the form of a dry powder preparation suitable for inhalation in which an ordered mixture may be formed between the active compounds and the pharmaceutically acceptable carrier.

Preferably at least 60% (such as at least 70% or at least 80% and more preferably at least 90%) of the total mass of active compounds (A) and (B) consists of particles having a diameter of less than about 10 microns, or of agglomerates of such particles, and, when the dry powder preparation comprises carrier other than when an ordered mixture is desired, preferably at least 60% (such as at least 70% or at least 80% and more preferably at least 90%) by mass of the total dry powder consists of particles having a diameter of less than about 10 microns, or of agglomerates of such particles.

While the dry powder for inhalation, whether with or without pharmaceutically acceptable carrier, may contain agglomerates of particles as indicated above, at the time of inhalation any agglomerates should be substantially deagglomerated yielding a powder of which at least 50% consists of particles having a diameter of up to 10 microns. The agglomerates can be the result of a controlled agglomeration process or they may simply be the result of the intimate contact of the powder particles. In either case it is essential that the agglomerates are capable of being de-agglomerated, e.g. by mechanical means in the inhaler or otherwise, into the aforesaid particles. Agglomerates are in general preferably not formed in the ordered mixture. In the case of an ordered mixture, the active compounds should be released from the large particles preferably upon inhalation, either by mechanical means in the inhaler or simply by the action of inhalation, or by other means, the active compounds then being deposited in the lower respiratory tract and the carrier particles in the mouth.

DETAILED DESCRIPTION

Any biologically active form or derivative of insulin may be used in the present invention. For example bovine, porcine, or biosynthetic or semisynthetic human insulin, or a biologically active derivative of human insulin ("modified insulin"), for example having certain amino acid substitutions as taught by Brange et al in "Diabetes Care" 13:923, 1990, may be used. Modified insulins are developed in order to improve various properties, for example to improve stability or give an improved pharmokinetic profile (i.e. improved profile of absorption through the epithelial membranes). The insulin should have a low zinc content, since zinc lowers the solubility of insulin, probably reducing the absorption rate, and also because zinc may form undesirable insoluble preciptates with certain of the enhancer substances for use in the present invention. In addition the insulin should be in the form of a dry powder which dissolves rapidly in aqueous solution.

The substance which enhances the absorption of insulin in the lung, hereinafter referred to as the enhancer, can be any of a number of compounds which act to enhance absorption through the layer of epithelial cells in the lower respiratory tract, and into the adjacent pulmonary vasculature. The enhancer can accomplish this by any of several possible mechanisms, including but not limited to the following:

(1) Enhancement of the paracellular permeability of insulin by inducing structural changes in the tight junctions between the epithelial cells.

(2) Enhancement of the transcellular permeability of insulin by interacting with or extracting protein or lipid constituents of the membrane, and thereby perturbing the membrane's integrity.

(3) Interaction between enhancer and insulin which increases the solubility of insulin in aqueous solution. This may occur by preventing formation of insulin aggregates (dimers, trimers, hexamers), or by solubilizing insulin molecules in enhancer micelles.

(4) Decreasing the viscosity of, or dissolving, the mucus barrier lining the alveoli and passages of the lung, thereby exposing the epithelial surface for direct absorption of the insulin.

Enhancers may function by only a single mechanism set forth above, or by two or more. An enhancer which acts by several mechanisms is more likely to promote efficient absorption of insulin than one which employs only one or two. For example, surfactants are a class of enhancers which-are believed to act by all four mechanisms listed above. Surfactants are amphiphilic molecules having both a lipophilic and a hydrophilic moiety, with varying balance between these two characteristics. If the molecule is very lipophilic, the low solubility of the substance in water may limit its usefulness. If the hydrophilic part overwhelmingly dominates, however, the surface active properties of the molecule may be minimal. To be effective, therefore, the surfactant must strike an appropriate balance between sufficient solubility and sufficient surface activity.

Another surfactant property that may be of importance is the net charge of the surfactant at the pH value in the lung (approximately 7.4). The isoelectric pH of insulin is 5.5. At pH 7.4, insulin has a negative net charge. This results in an electrostatic repulsion between insulin molecules, which in turn prevents aggregation and thereby increases the solubility. If the surfactant also is negatively charged, yet can interact with insulin by, for example, hydrophobic interactions, additional repulsion among the insulin molecules will occur. Therefore, an anionic surfactant will possess the additional advantage (compared to those having neutral or net positive charge at physiological pH) of enhancing absorption by helping stabilize insulin in the monomeric state.

A number of different compounds potentially useful as enhancers in the methods of the invention were tested in rats, as described in Example 5 below. Other substances with known absorption-enhancing properties, or with physical characteristics which make them likely candidates for use in the method of the invention, can be readily tested by one of ordinary skill in that in vivo assay, or alternatively in the in vitro assay described in Example 6.

It is possible that a combination of two or more enhancer substances will also give satisfactory results. The use of such a combination is considered to be within the invention.

An enhancer useful in the methods of the invention will combine effective enhancement of insulin absorption with (1) lack of toxicity in the concentrations used and (2) good powder properties, i.e., lack of a sticky or waxy consistency in the solid state. Toxicity of a given substance can be tested by standard means, such as by the MTT assay, for example as described in Int. J. Pharm., 65 (1990), 249–259. The powder properties of a given substance may be ascertained from published data on the substance, or empirically.

One very promising type of enhancer is the salt of a fatty acid. It has been found that the sodium salts of saturated fatty acids of carbon chain length 10 (i.e., sodium caprate), 12 (sodium laurate) and 14 (sodium myristate) perform well in the method of the invention. The potassium and lysine salts of capric acid have also been found to be effective in the method of the invention. If the carbon chain length is shorter than about 8, the surface activity of the surfactant may be too low, and if the chain length is longer than about 16, decreased solubility of the fatty acid salt in water limits its usefulness. Examples of preferred fatty acid salts are sodium, potassium and lysine salts of caprylic acid ($C_8$), capric acid, lauric acid, and myristic acid.

Most preferably in the present invention the substance which enhances the absorption of insulin in the lower respiratory tract is sodium caprate.

In a particularly preferred embodiment, the therapeutic preparation comprises active compounds (A) insulinand (B) sodium caprate, in the form of a dry powder suitable for inhalation in which at least 50% of the total mass of active compounds (A) and (B) consists of (a) primary particles having a diameter of less than about 10 microns, for example between 0.01 and 10 microns and preferably between 1 and 6 microns, or (b) agglomerates of such particles; specifically, in this particularly preferred embodiment this invention provides:

a therapeutic preparation of insulin and sodium caprate, which preparation is in the form of a dry powder suitable for inhalation of which at least 50% by mass consists of (a) particles having a diameter of less than about 10 microns or (b) agglomerates of said particles;

a therapeutic preparation comprising insulin, sodium caprate and a pharmaceutically acceptable carrier, which preparation is in the form of a dry powder suitable for inhalation of which at least 50% by mass consists of (a) particles having a diameter of less than about 10 microns, or (b) agglomerates of said particles; and a therapeutic preparation comprising active compounds (A) insulin and (B) sodium caprate, wherein at least 50% of the total mass of active compounds (A) and (B) consists of particles having a diameter of less than about microns, and a pharmaceutically acceptable carrier, which preparation is in the form of a dry powder preparation suitable for inhalation in which an ordered mixture may be formed between the active compounds and the pharmaceutically acceptable carrier.

Different counterions may change the solubility of the saturated fatty acid salt in water, such that an enhancer having a carbon length other than 8–16 would prove even more advantageous than the enhancers specifically mentioned hereinabove. Salts of unsaturated fatty acids may also-be useful in the present invention since they are more water soluble than salts of saturated fatty acids, and can therefore have a longer chain length than the latter and still maintain the solubility necessary for a successful enhancer of insulin absorption.

Bile salts and bile salt derivatives were tested for usefulness as enhancers in the method of the present invention. All of those tested (sodium salts of ursodeoxycholic acid, taurocholic acid, glycocholic acid, and taurodihydrofusidic acid) effectively enhance insulin absorption in the lung. Examples of suitable bile salts include salts (e.g., sodium or potassium salts) of cholic acid, chenodeoxycholic acid, glycocholic acid, taurocholic acid, glycochenodeoxycholic acid, taurochenodeoxycholic acid, deoxycholic acid, glycodeoxycholic acid, taurodeoxycholic acid, lithocholic acid, and ursodeoxycholic acid. Preferred are the trihydroxy bile salts, such as the salts (e.g., potassium and sodium salts) of cholic, glycocholic and taurocholic acids. Particularly preferred are sodium taurocholate and potassium taurocholate.

Phospholipids were also tested as enhancers. It was found that a single-chain phospholipid (lysophosphatidylcholine) was an effective enhancer, while one double-chain phospholipid (didecanoylphosphatidylcholine) was not. This may be explained by the fact that the double-chain phospholipid is much less soluble in water than its single-chain counterpart; however, it is reasonable to expect that double-chain phospholipids of shorter chain length, having greater water-solublility than their longer chain counterparts, will be of use as enhancers in the present invention so that both single- and double-chain phospholipids may be used. Examples of single-chain phospholipids include lysophosphatidylcholine, lysophosphatidylglycerol, palmitoylphosphatidylglycerol, palmitoylphosphatidylcholine, lysophosphatidylethanolamine, lysophosphatidylinositol, and lysophosphatidylserine. Examples of double-chain phospholipids include diacylphosphatidylcholine, diacylphosphatidylglycerol, diacylphosphatidylethanolamine, diacylphosphatidylinositol, and diacylphosphatidylserine.

One glycoside, octylglucopyranoside, was tested as an enhancer in the present invention and was found to have some absorption enhancing properties. Other alkyl glycosides such as the alkyl glucosides (e.g., decyl glucoside, dodecyl glucoside, and alkyl thioglucopyranoside) and alkyl maltosides (e.g., decyl maltoside and dodecyl maltoside) would also be expected to exhibit absorption enhancing properties in the methods of the present invention.

The cyclodextrins and derivatives thereof effectively enhance the nasal absorption of insulin, and may function similarly in the lung. Dimethyl-β-cyclodextrin has been tested in the method of the present invention and has been found to have an absorption enhancing effect.

Other potentially useful surfactants are sodium salicylate, sodium 5-methoxysalicylate, and the naturally occurring surfactants such as salts (e.g., sodium or potassium salts) of glycyrrhizine acid, saponin glycosides, and acyl camitines such as decanoyl camitine, lauroyl carnitine, myristoyl carnitine, and palmitoyl camitine.

For ionic enhancers (e.g., the anionic surfactants described above), the nature of the counterion may be important. The particular counterion selected may influence the powder properties, solubility, stability, hygroscopicity, and local/systemic toxicity of the enhancer or of any formulation containing the enhancer. It may also affect the stability and/or solubility of the insulin with which it is combined. In general, it is expected that monovalent metallic cations such as sodium, potassium, lithium, rubidium, and cesium will be useful as counterions for anionic enhancers. Ammonia and organic amines form another class of cations that is expected to be appropriate for use with anionic enhancers having a carboxylic acid moiety. Examples of such organic amines include ethanolamine, diethanolamine, triethanolamine, 2-amino-2-methylethylamine, betaines, ethylenediamine, N,N-dibensylethylenetetraamine, arginine, hexamethylenetetraamine, histidine, N-methylpiperidine, lysine, piperazine, spermidine, spermine and tris (hydroxymethyl)aminomethane.

Since effective enhancement of insulin absorption in the lung was observed for a number of the enhancers tested, it is expected that many more will be found which also function in this manner. Starch microspheres effectively enhance the bioavailability of insulin delivered via the nasal membranes and were tested as an enhancer in the methods of the invention. Although they proved to be of little use for delivery via the pulmonary route in the animal model utilized herein, it is thought that this was mainly due to technical difficulties which, if overcome, may lead to successful delivery via the pulmonary route. Chelators are a class of enhancers that are believed to act by binding calcium ions. Since calcium ions help maintain the dimensions of the space between cells and additionally reduce the solubility of insulin, binding of these ions would in theory both increase the solubility of insulin, and increase the paracellular permeability of insulin. Although one chelator tested, the sodium salt of ethylenediaminetetraacetic acid (EDTA), was found to be ineffective in enhancing absorption of insulin in the rat model tested, other calcium ion-binding chelating agents may prove to be more useful.

In general, it is desirable to keep the ratio of insulin to enhancer as high as possible, within the range that permits fast and efficient enhancement of insulin absorption. This is important in order to minimize the risk of adverse effects, both local and systemic, attributable to the enhancer. The optimal ratio of insulin to enhancer can be ascertained for any given enhancer by testing various proportions in in vivo models such as described herein. For example, insulin was combined with sodium caprate in the following w/w proportions: 50/50, 75/25, 82.5/17.5, and 90/10. Significant improvement in absorption of insulin was obtained with 50% and 25% sodium caprate; 10% gave poor improvement in absorption, and the results with 17.5% were intermediate. This indicates that the lowest effective concentration of sodium caprate for use in the methods of the invention is approximately 15–25%, and probably 20–25%. Other enhancers may have higher or lower optimal concentrations relative to insulin, and each individual enhancer must therefore be separately tested. Based upon the above results, however, it is expected that the optimal proportion of a surfactant type of enhancer will generally be between 10 and 50% of the insulin/enhancer mixture, for example between 15% and 50% (such as between 25% and 50%). It should be noted that the above proportions represent the proportion of enhancer relative solely to insulin, and do not take into account any carrier or other additive which may be added, for example to improve the powder properties of the formulation.

The amount of insulin absorbed according to the present invention can be significantly higher than the amount absorbed in the absence of enhancer. In Example 4 herein it is shown that a therapeutic preparation according to the present invention, when inhaled, exhibits a bioavailability well over three times greater than that of an inhaled preparation of insulin alone.

Preferably the amount of insulin absorbed according to the present invention is significantly ($p<0.05$) higher than the amount absorbed in the absence of enhancer.

As stated hereinabove, additive substances commonly included in therapeutic preparations, such as pharmaceutically acceptable carriers, may be included in the theraputic preparation of the present invention. Additive substances may be included, for example, in order to dilute the powder to an amount which is suitable for delivery from the particular intended powder inhaler; to facilitate the processing of the preparation; to improve the powder properties of the preparation; to improve the stability of the preparation, e.g. by means of antioxidants or pH-adjusting compounds; or to add a taste to the preparation. Any additive should not adversely affect the stability of the insulin or absorption enhancer, or disadvantageously interfere with the insulin absorption. It should also be stable, not hygroscopic, have good powder properties and haveno adverse effects in the airways. Examples of potential additives include mono-, di-, and polysaccharides, sugar alcohols and other polyols, such as for example lactose, glucose, raffinose, melezitose, lactitol, maltitol, trehalose, sucrose, mannitol and starch. As reducing sugars such as lactose and glucose have a tendency to form complexes with proteins, non-reducing sugars such as raffinose, melezitose, lactitol, maltitol, trehalose, sucrose, mannitol and starch may be preferred additives for use in the present invention. Depending upon the inhaler to be used, the total amount of such additives may vary over a very wide range. In some circumstances little or no additive would be required, whereas for example in the case of an inhaler requiring large powder volumes for operation, a very high percentage of the therapeutic preparation could consist of additive. The amount of additive desirable would be easily determined by a person skilled in the art according to particular circumstances.

A useful mechanism for delivery of the powder into the lungs of a patient is through a portable inhaler device suitable for dry powder inhalation. Many such devices, typically designed to deliver antiasthmatic or antiinflammatory agents into the respiratory system, are on the market.

Preferably the device is a dry powder inhaler of a design which provides protection of the powder from moisture and has no risk of delivering overly large doses; in addition as many as possible of the following are desired: protection of the powder from light; high respirable fraction and high lung deposition in a broad flow rate interval; low deviation of dose and respirable fraction; low retention of powder in the mouthpiece; low adsorption to the inhaler surfaces; flexibility in dose size; and low inhalation resistance. The inhaler is preferably a single dose inhaler, although a multi dose inhaler, preferably such as a multi dose, breath actuated, dry powder inhaler for multiple use, may also be employed. Preferably the inhaler used is a unit dose, breath actuated, dry powder inhaler for single use.

The described powder preparation can be manufactured in several ways, using conventional techniques. It may be necessary to micronize the active compounds and if appropriate (i.e where an ordered mixture is not intended) any carrier in a suitable mill, for example in a jet mill at some point in the process, in order to produce primary particles in a size range appropriate for maximal deposition in the lower respiratory tract (i.e., under 10 $\mu$m). For example, one can dry mix insulin and enhancer powders, and carrier where appropriate, and then micronize the substances together; alternatively, the substances can be micronized separately, and then mixed. Where the compounds to be mixed have different physical properties such as hardness and brittleness, resistance to micronisation varies and they may require different pressures to be broken down to suitable particle sizes. When micronised together, therefore, the obtained particle size of one of the components may be unsatisfactory. In such case it would be advantageous to micronise the different components separately and then mix them.

It is also possible first to dissolve the components including, where an ordered mixture is not intended, any carrier in a suitable solvent, e.g. water, to obtain mixing on the molecular level. This procedure also makes it possible to adjust the pH-value to a desired level. It is known that the nasal absorption of insulin is affected by the pH-value of the preparation, with increasing absorption when moving either up or down from the isoelectric point of insulin, which is around 5.5. However, the insulin may be less stable at pH significantly above or below 5.5, and furthermore the pharmaceutically accepted limits of pH 3.0 to 8.5 for inhalation products must be taken into account, since products with a pH outside these limits may induce irritation and constriction of the airways. To obtain a powder, the solvent must be removed by a process which retains the insulin's biological activity. Suitable drying methods include vacuum concentration, open drying, spray drying, and freeze drying. Temperatures over 40° C. for more than a few minutes should generally be avoided, as some degradation of the insulin may occur. Following the drying step, the solid material can, if necessary, be ground to obtain a coarse powder, then, if necessary, micronized.

If desired, the micronized powder can be processed to improve the flow properties, e.g., by dry granulation to form spherical agglomerates with superior handling characteristics, before it is incorporated into the intended inhaler device. In such a case, the device would be configured to ensure that the agglomerates are substantially deagglomerated prior to exiting the device, so that the particles entering the respiratory tract of the patient are largely within the desired size range.

Where an ordered mixture is desired, the active compound may be processed, for example by micronisation, in order to obtain particles within a particular size range. The carrier may also be processed, for example to obtain a desired size and desirable surface properties, such as a particular surface to weight ratio, or a certain ruggedness, and to ensure optimal adhesion forces in the ordered mixture. Such physical requirements of an ordered mixture are well known, as are the various means of obtaining an ordered mixture which fulfills the requirements, and may be determined easily by the skilled person according to the particular circumstances.

The invention will now be described by way of Examples, which are intended to illustrate but not limit the scope of the invention.

EXAMPLES

COMPARATIVE EXAMPLE

Therapeutic Preparation of Insulin Without Enhancer

Semisynthetic human insulin (Diosynth, 0.8 g) and water (150 ml) were added to a beaker. The pH was lowered with 1 M HCl to pH 3.4 and then raised with 1 M NaOH to pH 7.4, in order to dissolve the insulin.

Lactose (commercially available, 9.2 g) was added and the pH again adjusted to pH 7.4. The solution was stirred until clear or weakly opalescent, and concentrated by evaporation, at a temperature of 37° C. over a period of about two days.

The obtained solid cake was crushed, and sieved through a 0.5 mm sieve, and the resultant powder micronised through a jet mill to particles with a diameter of about 2 microns.

Example 1

Therapeutic Preparation of Insulin and Sodium Caprate; Ratio 75:25

Semisynthetic human insulin (9.75 g) and water (250 ml) were added to a beaker. The pH was lowered-with 1 M HCl to pH 3.4 and then raised with 1 M NaOH to pH 7.4, in order to dissolve the insulin.

Sodium caprate (Sigma, 3.25 g) was added and the pH again adjusted to pH 7.4. The solution was stirred until clear or weakly opalescent, and concentrated by evaporation, at a temperature of 37° C. over a period of about two days.

The obtained solid cake was crushed, and sieved through a 0.5 mm sieve, and the resultant powder micronised through a jet mill to particles of about 2 microns diameter.

Example 2

Therapeutic Preparation of Insulin and Sodium Cadrate, with Lactose: Ratio 50:25:25

Semisynthetic human insulin (7.5 g) was dissolved in water (150 ml) as in Example 1. Sodium caprate (3.75 g) and lactose (3.75 g) were added and the procedure of Example 1 followed to produce a powder largely consisting of particles with a diameter of about 2 microns.

Example 3

Therapeutic Preparation of Insulin and Sodium Caprate, with Lactose; Ratio 4:4:92

The procedure of Example 2 was followed, using 0.5 g of semisynthetic human insulin, 150 ml water, 0.5 g sodium caprate and 11.5 g lactose.

Inhalation Studies

Study 1

The preparation of Example 1 was used in an inhalation study in two dogs. The preparation was filled into a Wright Dust Feed inhalation apparatus and administered to the dogs. The dosage level was 1 U./kg (1 U.=one unit of human insulin=35 µg human insulin, 100%) Blood glucose and plasma insulin values were measured at various time intervals and the results are summarised in Tables 1 and 2 below.

TABLE I

| Blood sample time after end of exposure (minutes) | Blood glucose (mmol/L) | Insulin conc. (µU/ml) |
| --- | --- | --- |
| before | 3.9 | 6.70 |
| 0.5 | 3.6 | 120.66 |
| 5 | 2.8 | 194.47 |
| 10 | 2.6 | 195.39 |
| 20 | n.d | 139.74 |
| 22.5 | 1.6 | n.d |
| 31 | 2.0 | 73.42 |
| 45 | 1.7 | 47.49 |
| 59.5 | 1.7 | 36.21 |
| 89.5 | 2.3 | 19.28 |
| 120 | 3.0 | 14.58 |
| 240 | 4.5 | 5.28 | n.d. = not determined

TABLE II

| Blood sample time after end of exposure (minutes) | Blood glucose (mmol/L) | Insulin conc. (µU/ml) |
| --- | --- | --- |
| before | 3.9 | 44.84 |
| 3 | 4.2 | 165.10 |
| 6 | 4.3 | 158.28 |
| 12 | 3.9 | n.d. |
| 14 | n.d. | 180.72 |
| 19 | 3.0 | 133.75 |
| 30 | 2.7 | 143.71 |
| 45 | 2.5 | 91.62 |
| 60 | 2.4 | 66.70 |
| 90 | 2.7 | 38.58 |
| 122 | 3.7 | 29.15 |
| 241 | 4.1 | n.d. |
| 242.5 | n.d. | 19.76 | n.d. not determined

The tables illustrate that the insulin/sodium caprate formulation markedly increases the plasma level of insulin and decreases the blood glucose. The peak value for plasma insulin and the minimal value for blood glucose are reached after approximately 15 and 60 minutes, respectively.

Study 2

Figure 1:
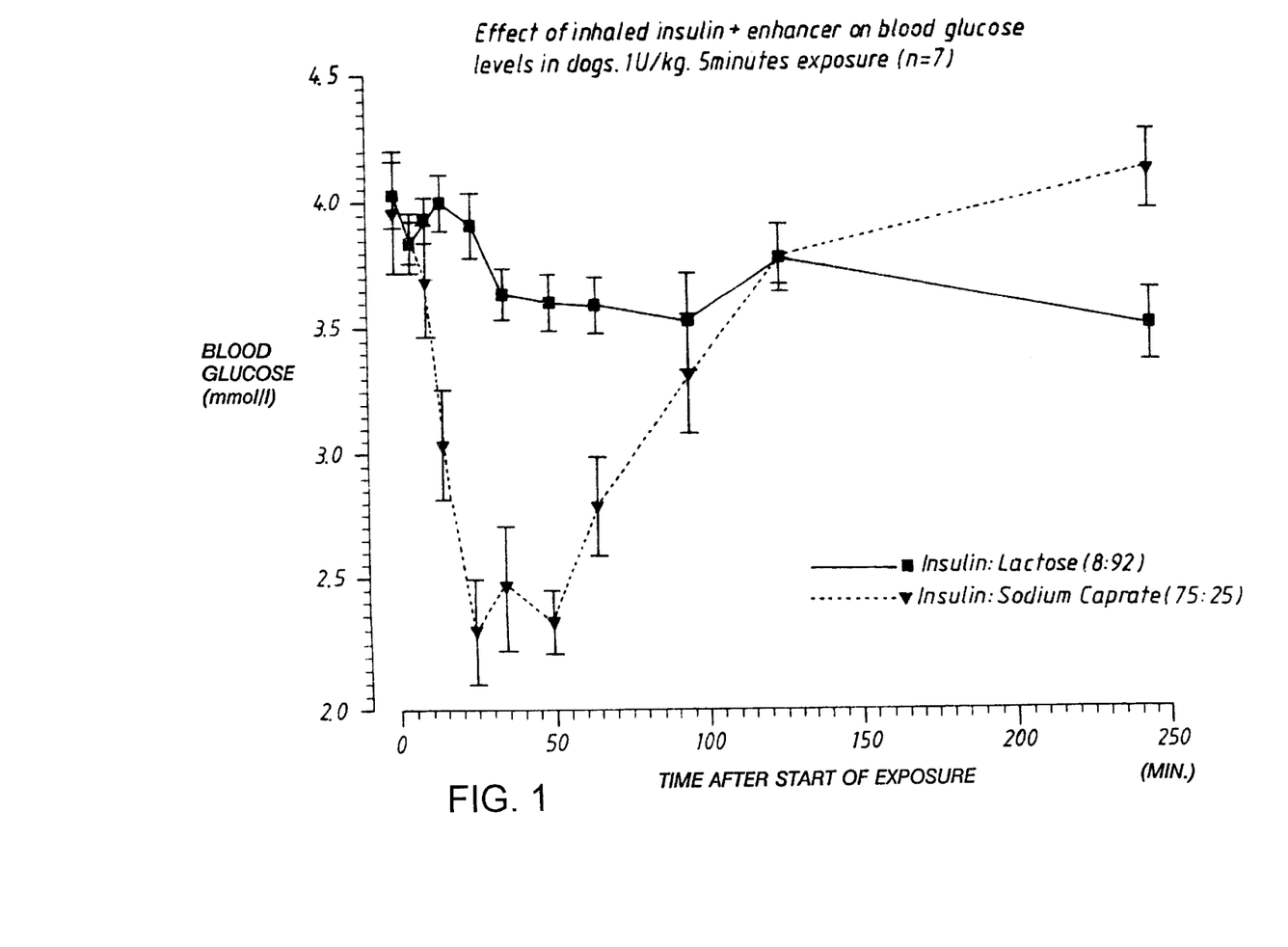
FIG. 1 is a graph comparing the effect of inhaled insulin plus enhancer to the effect of inhaled insulin without enhancer in blood glucose levels in a dog.
Figure 2:
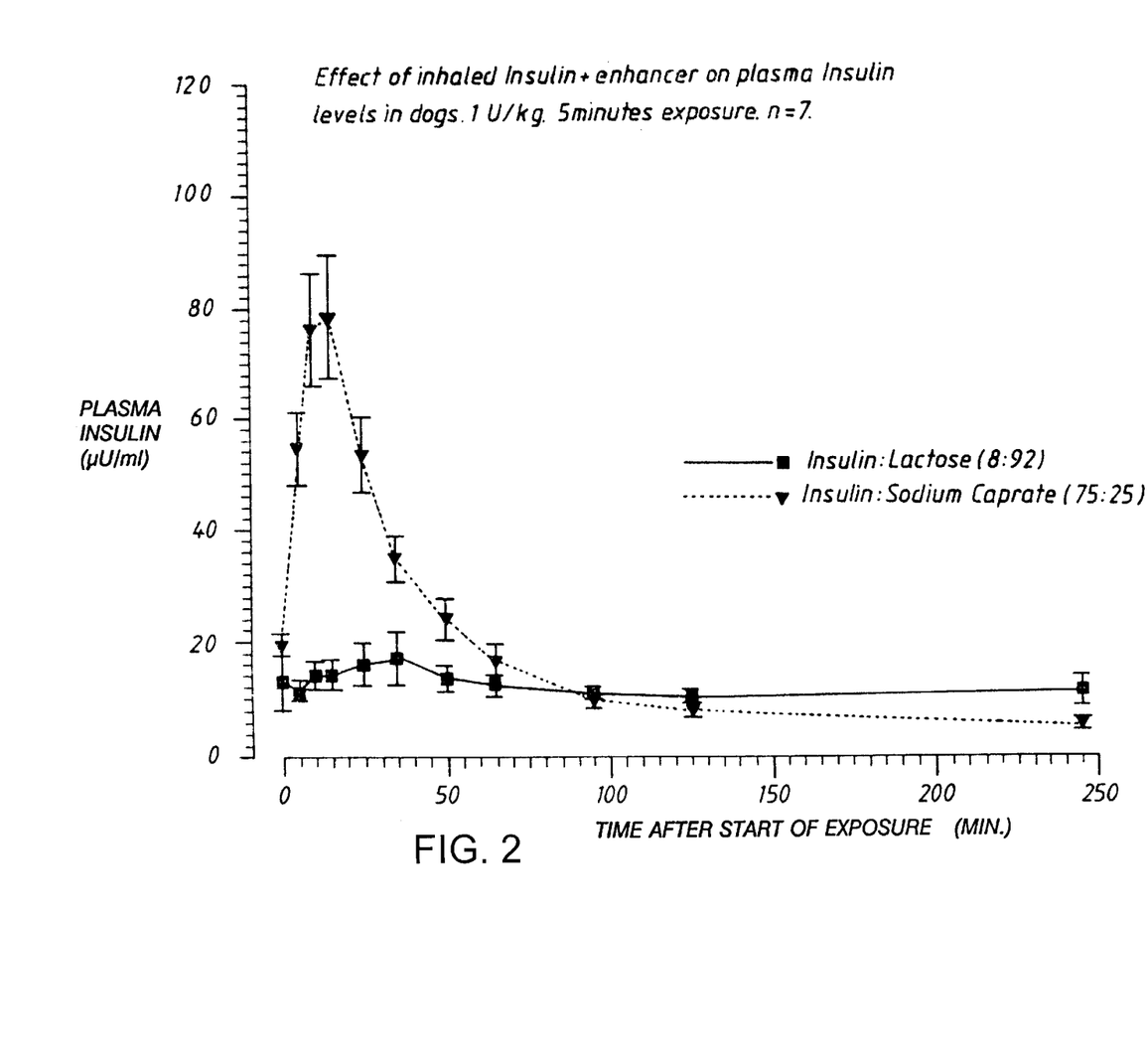
FIG. 2 is a graph comparing the effect of inhaled insulin plus enhancer to the effect of inhaled insulin without enhancer on blood glucose levels in a second dog.
Figure 3:
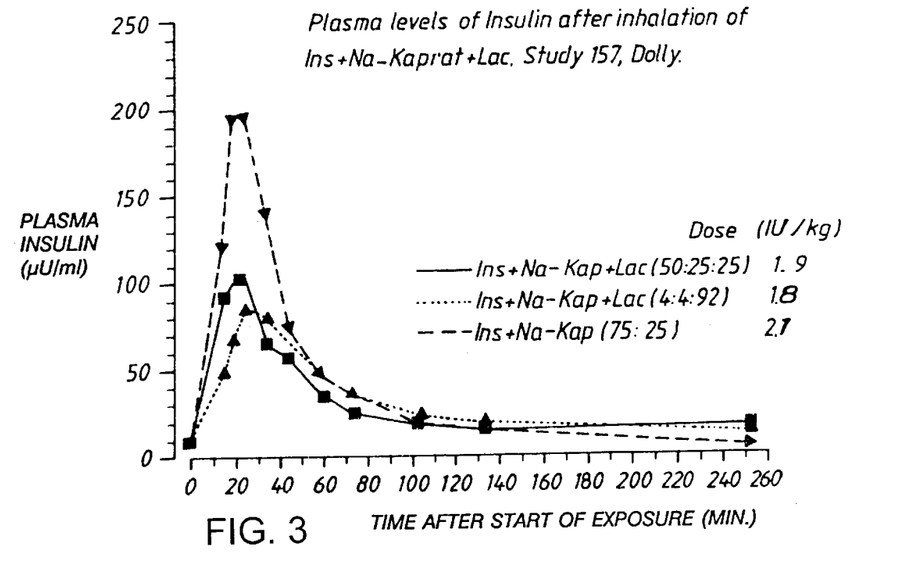
FIG. 3 is a graph comparing plasma levels of insulin after inhalation of three different formulations of insulin and enhancer in a dog.
Figure 4:
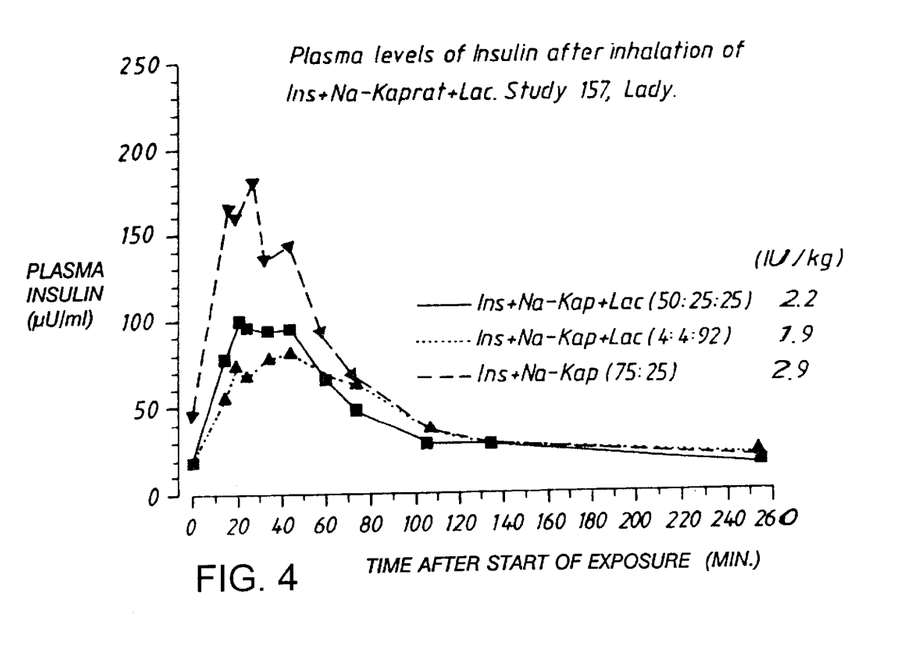
FIG. 4 is a graph comparing plasma levels of insulin after inhalation of three different formulations of insulin and enhancer in a second dog.

The preparations of the Comparative Example and Example 1 were each administered to four or five dogs, by means of a Wright Dust Feed inhalation apparatus, at a constant dosage level of 1 U./kg. The effect of each formulation on plasma insulin levels and blood glucose levels.was determined at various time points and the results are illustrated in FIGS. 1 and 2. It was found that, while the control formulation containing no enhancer produced essentially no change in plasma insulin levels, the formulation containing both insulin and enhancer produced a rise in plasma insulin levels from about 20 µU/ml at time zero to about 80 µU/ml 15 min. after inhalation of the powder. Likewise, the control animals registered a maximal drop in blood glucose of about 0.5 mmol/l following inhalation of insulin without enhancer, while the animals which inhaled insulin plus enhancer registered a transient drop of about 1.7 mmol/l, from about 4.0 mmol/l to about 2.3 mmol/l. Thus, insulin combined with the enhancer, sodium caprate, was quickly absorbed into and cleared from the systemic circulation, with a corresponding transient decrease in blood glucose levels. In contrast, insulin with carrier (lactose) but no enhancer was detectably absorbed only to a very small degree. (p=0.0002 for insulin/ caprate vs. insulin/lactose.)

Study 3

The preparations of Examples 1–3 were each tested at varying dosage levels in two dogs. Administration of the preparations was by means of a Wright Dust Feed inhalation apparatus. Plasma insulin and blood glucose levels were measured at various time intervals following inhalation. The results are indicated in FIGS. 3–6, and show that insulin combined with sodium caprate in various proportions absorbs quickly, and that peak values are obtained after 20–30 minutes, followed by corresponding decreases in blood glucose levels. The results also indicate that by inhalation of insulin powder a plasma profile can be obtained which is more like the natural physiological profile than the profile obtained after subcutaneous injection of insulin.

Example 4

Insulin and Sodium Caprate, 75:25; Mixing of Micronised Powders

Biosynthetic human insulin (53 g) was micronised in an Airfilco Jet Mill (Trade Mark, Airfilco Process Plant Limited), with pressurised nitrogen (feed pressure 7 bar, chamber pressure 5 bar), to a mass median diameter of 2.4 micrometers.

Sodium caprate (170 g) was micronised in an Airfilco. Jet Mill (TM), with pressurised nitrogen (feed pressure 5 bar, chamber pressure 3 bar), to a mass median diameter of 1.6 micrometers.

The micronised biosynthetic human insulin (45 g) and sodium caprate (14.26 g) were dry mixed according to the following procedure: Half of the insulin was added to a mixing device comprising a mixing cylinder of volume 4.4 litres divided, by a sieve of width 1 mm, into two compartments, with a metal ring in each compartment to aid mixing and stirring. The sodium caprate and finally the rest of the insulin, were added. The mixing cylinder was closed, turned 180 degrees, and mounted in a motorised shaking apparatus. The motor was turned on and shaking continued for approximately two minutes, until all the insulin and sodium caprate had passed through the sieve. The motor was turned off and the mixing cylinder turned 180 degrees, again mounted on the shaking apparatus and shaking was again effected until all the powder had passed through the sieve. This procedure was repeated a further eight times to give a total mixing time of approximately 20 minutes.

The preparation so obtained was administered to 5 dogs by inhalation, using a Wright Dust Feed inhalation apparatus, at a dosage level of 1 U./kg, and the plasma insulin level determined at various time points after administration.

The results obtained were compared with the plasma insulin levels obtained when biosynthetic insulin, micronised as above to a mass median diameter of 2.4 micrometers, were administered to five dogs in the same way and at the same dosage levels, and with the plasma insulin levels obtained when a therapeutic preparation of insulin and sodium caprate in a ratio of 90:10 was administered to five dogs in the same way and at the same dosage levels as above. In this case the therapeutic preparation was prepared as follows: Human semisynthetic insulin was gel filtrated to reduce the zinc content from 0.52% to 0.01% relative to content of insulin. Insulin (4.5 g) and sodium caprate (0.5 g) were dissolved in water (232 ml). The solution was stirred until clear and the pH adjusted to 7.0. The solution was concentrated by evaporation at 37° C. over a period of about two days. The obtained solid cake was crushed, and sieved through a 0.5 mm sieve, and the resultant powder micronised through a jet mill to particles with a mass median diameter of 3.1 micrometers.

Figure 9:
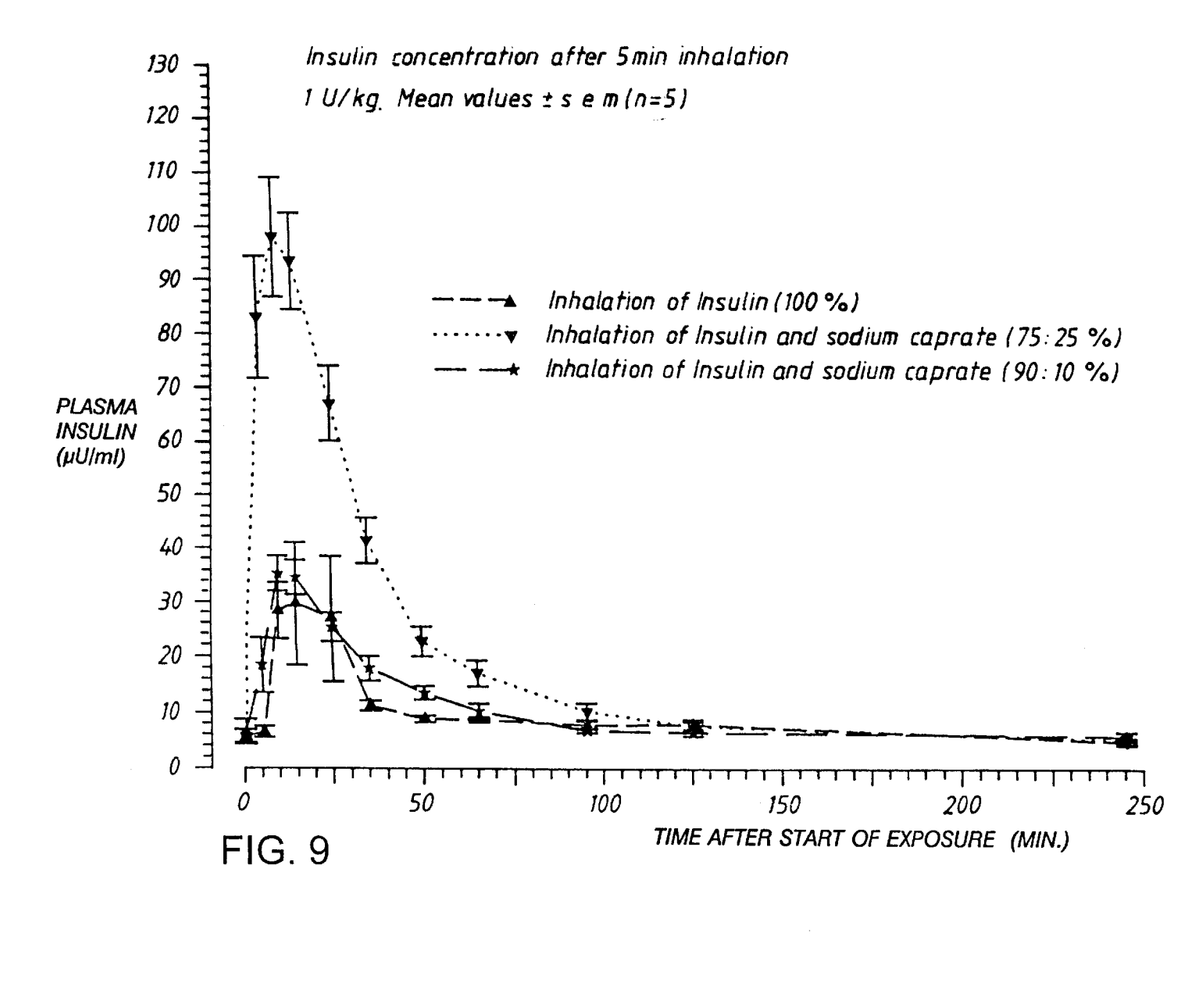
FIG. 9 is a graph comparing plasma insulin levels following inhalation of insulin alone, or insulin:sodium caprate 75:25 or 90:10.

The results of these comparisons are presented in FIG. 9. The results demonstrate some improvement in the bioavailability of insulin with the 90:10 formulation, and a dramatic improvement in the bioavailability of insulin with the 75:25 preparation according to the present invention, as compared to insulin alone. (p=0.0147 for the difference between 75:25 and 100:0).

Example 5

Selection of Enhancers

Each of the compounds listed in Table III was tested for its ability to enhance uptake of insulin, and thus affect blood glucose levels, in a rat model. Various forms of insulin were employed: recombinant or semisynthetic human or bovine. Each formulation was prepared as in Examples 1–3 above, drying and processing the insulin/enhancer solution to produce an inhalable powder.

The powder was administered to rats by inhalation, and the blood glucose levels of the rats were subsequently monitored. These levels were compared to the corresponding values obtained from rats which had inhaled insulin formulations without enhancer.

TABLE III

| Substance | Enhancer: Insulin: lactose | Effect |
| --- | --- | --- |
| Octylglucopyranoside | 4:4:92 | (+) |
| Sodium ursodeoxycholate | 4:4:92 | + |
| Sodium taurocholate | 4:4:92 | + |
| Sodium glycocholate | 4:4:92 | + |
| Lysophosphatidylcholine | 4:4:92 | + |
| Dioctanoylphosphatidylcholine | 2:4:94 | (+) |
| Didecanoylphospatidylcholine | 4:4:94 | − |
| Sodium taurodihydrofusidate | 2:4:94 | + |
| Sodium caprylate | 25:75:0 | + |
| Sodium caprate | 10:90:0 | (+) |
| Sodium caprate | 17.5:82.5:0 | (+) |
| Sodium caprate | 25:75:0 | + |
| Sodium caprate | 4:4:92 | + |
| Sodium laurate | 25:75:0 | (+) |
| Potassium oleate | 4:4:92 | + |
| Potassium caprate | 27:73:0 | + |

TABLE III-continued

| Substance | Enhancer: Insulin: lactose | Effect |
| --- | --- | --- |
| Lysine caprate | 35:65:0 | + |
| Sodium myristate | 30:70:0 | + |
| Dimethyl-β-cyclodextrin | 75:25:0 | + |

+ significant decrease in blood glucose level
(+) moderate decrease in blood glucose level
− no or very small decrease in blood glucose level Example 6

Selection of Enhancers

Figure 5:
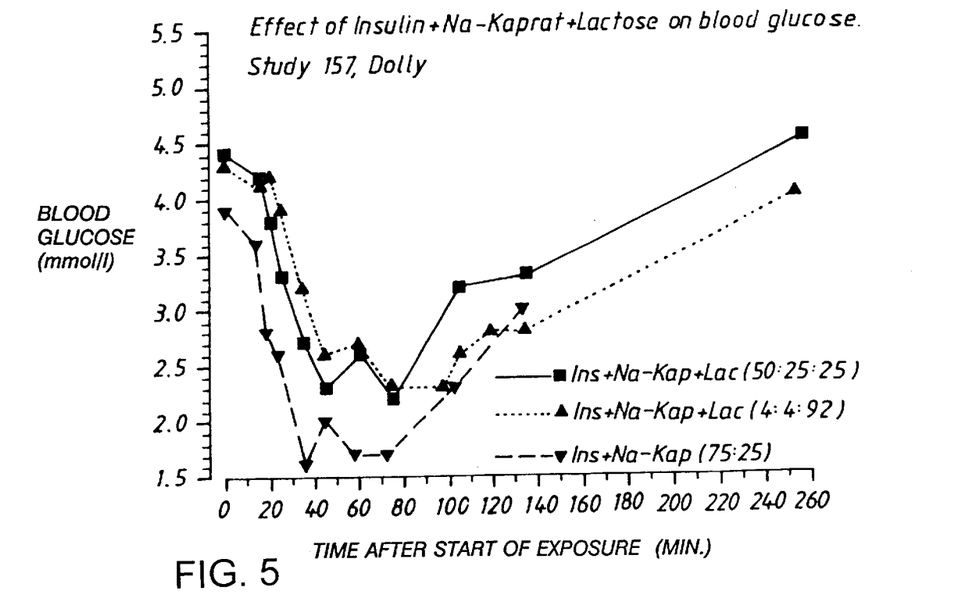
FIG. 5 is a graph comparing blood glucose levels following inhalation of three different formulations of insulin and enhancer in a dog.
Figure 6:
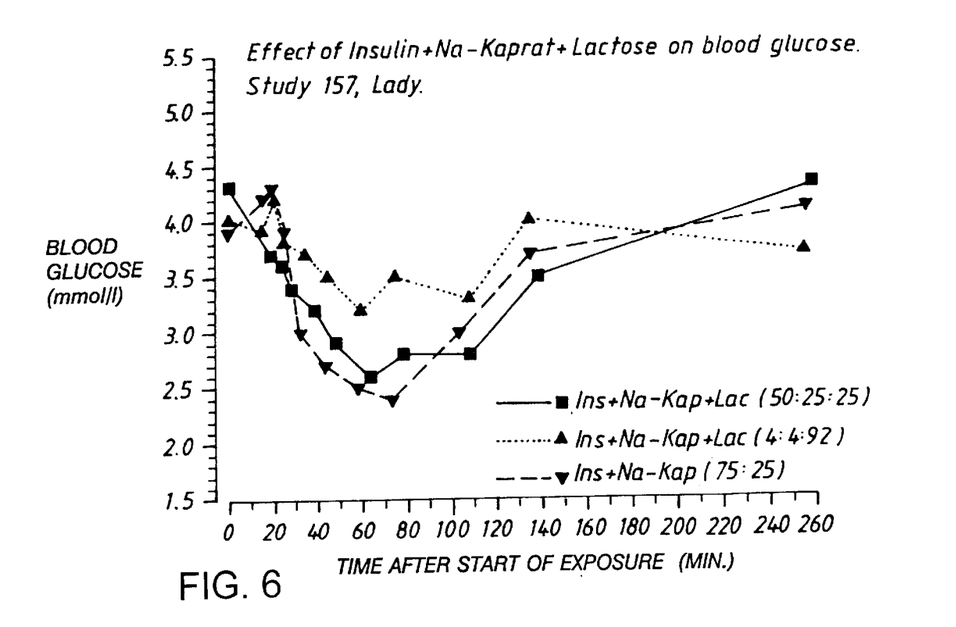
FIG. 6 is a graph comparing blood glucose levels following inhalation of three different formulations of insulin and enhancer in a second dog.
Figure 7:
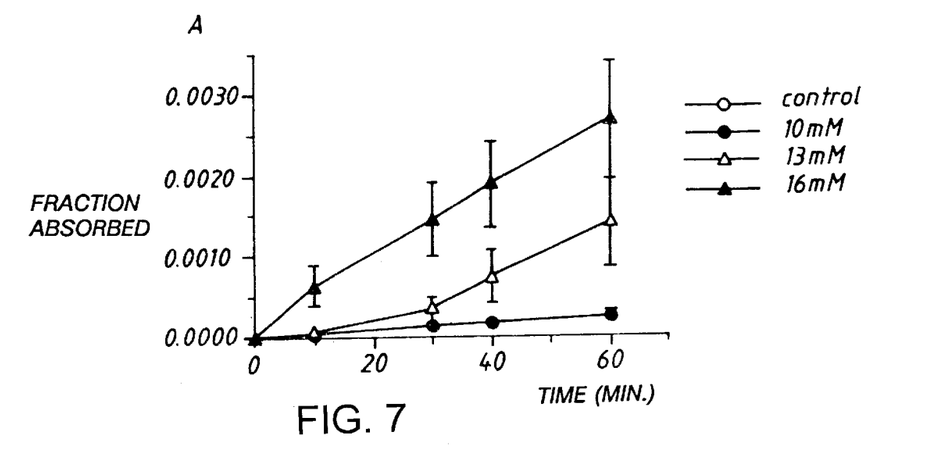
FIG. 7 is a graph showing the effect of three different concentrations of enhancer on transport of mannitol across a Caco-2 cell monolayer.
Figure 8:
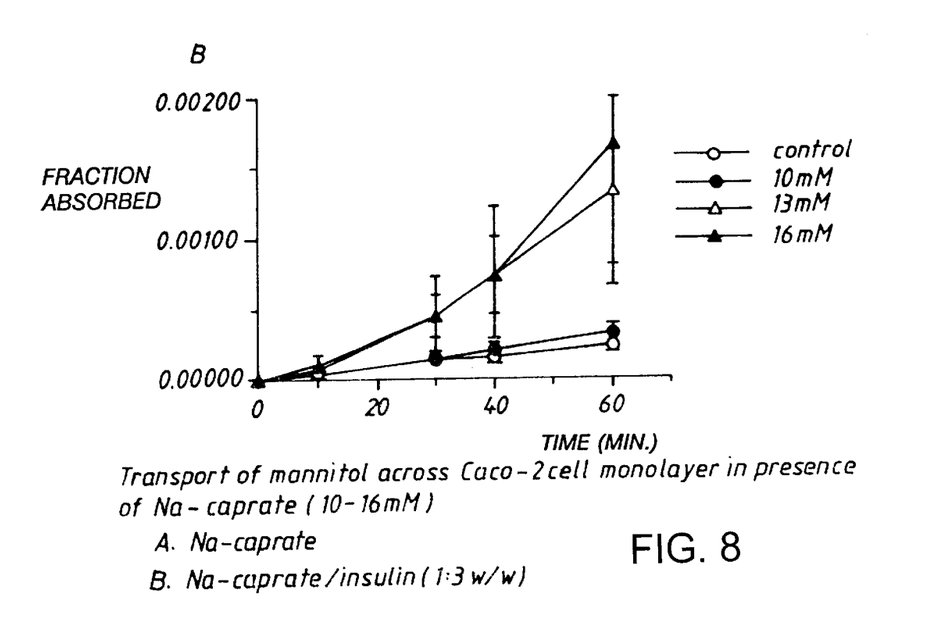
FIG. 8 is a graph showing the effect of three different concentrations of enhancer on transport of mannitol across a Caco-2 cell monolayer, in the presence of insulin.

A standard in vitro assay utilizing an epithelial cell line, CaCo-2 (available through the American Type Culture Collection (ATCC), Rockville, Md., USA), has been developed to assess the ability of various enhancer compounds to promote transport of insulin and other markers across an epithelial cell monolayer, as a model for the epithelial cell layer which functions in the lung to separate the alveolus from the pulmonary blood supply. In this assay, the enhancer and insulin or other marker are dissolved in aqueous solution at various proportions and/or concentrations, and applied to the apical side of the cell monolayer. After 60 min incubation at 37° C. and 95% RH (relative humidity), the amount of the marker on the basolateral side of the cells is determined: for example, by use of a radioactively labelled marker. For the particular enhancer (sodium caprate) tested in the experiments shown in FIGS. 5 and 6, the amount of marker (mannitol, MW 360) which appears on the basolateral side is dependent upon the concentration of enhancer used, at least up to 16 mM sodium caprate (FIG. 7). This is true even when insulin is added to the enhancer/mannitol mixture (1:3 sodium caprate:insulin, by weight) (FIG. 8). This concentration of sodium caprate (16 mM) was also found to promote absorption of insulin across the cell monolayer. The amount of insulin which passed across the monolayer doubled in the presence of 16 mM sodium caprate, compared to the amount in the absence of any enhancer. It is expected that at higher concentrations of sodium caprate, the permeability of the cells will be further increased; however, the potential cytotoxicity of sodium caprate may prevent the use of substantially higher concentrations of this particular enhancer.

This in vitro model of epithelial cell permeability can be used as a screening tool for rapidly testing any desired enhancer for usefulness in the methods of the invention.

What is claimed is:

1. A dry powder inhaler device containing a therapeutic preparation comprising active compounds (A) insulin and (B) a substance which enhances the absorption of insulin in the lower respiratory tract, in the form of a dry powder suitable for inhalation in which at least 50% of the total mass of active compounds consists of (a) particles having a diameter of up to 10 microns or (b) agglomerates of such particles, provided that said substance is selected from the group consisting of a $C_8$–$C_{16}$ fatty acid, a salt of such a fatty acid, a phospholipid, and an alkyl glycoside.

2. The dry powder inhaler device of claim 1, wherein the therapeutic preparation contains only said active compounds.

3. The dry powder inhaler device of claim 1, wherein the dry powder contains, in addition to said active compounds, a pharmaceutically acceptable carrier.

4. The dry powder inhaler device of claim 1, wherein said substance is a sodium, potassium or lysine salt of caprylic acid ($C_8$), capric acid ($C_{10}$), lauric acid ($C_{12}$), or myristic acid ($C_{14}$).

5. The dry powder inhaler device of claim 1, wherein said substance is a single- or double-chain phospholipid.

6. The dry powder inhaler device of claim 1, wherein said substance is selected from the group-consisting of lysophosphatidylcholine, lysophosphatidylglycerol, lysophosphatidylethanolamine, lysophosphatidylinositol, lysophosphatidylserine, diacylphosphatidylcholine, diacylphosphatidylglycerol, diacylphosphatidylethanolamine, diacylphosphatidylinositol, and diacylphosphatidylserine.

7. The dry powder inhaler device of claim 1, wherein said substance is palmitoylphosphatidylglycerol, palmitoylphosphatidylcholine, dioctanoylphosphatidylglycerol or dioctanoylphosphatidylcholine.

8. The dry powder inhaler device of claim 1, wherein said substance is an alkyl glucoside or alkyl maltoside.

9. The dry powder inhaler device of claim 1, wherein said substance is decyl glucoside, dodecyl glucoside, decyl maltoside, or dodecyl maltoside.

10. The dry powder inhaler device of claim 1, in which at least 50% of the dry powder consists of (a) particles having a diameter of between 1 and 6 microns or (b) agglomerates of such particles.

11. The dry powder inhaler device of claim 1, wherein the ratio of (A) to (B) in said preparation is in the range of 9:1 to 1:1.

12. A dry powder inhaler device comprising active compounds (A) insulin and (B) a substance which enhances the absorption of insulin in the lower respiratory tract, in the form of a dry powder suitable for inhalation in which at least 50% of the total mass of active compounds consists of (a) particles having a diameter of up to 10 microns or (b) agglomerates of such particles, provided that said substance is selected from the group consisting of a $C_8$–$C_{12}$ fatty acid, a salt of such a fatty acid, a phospholipid, and an alkyl glycoside.

13. The dry powder inhaler device of claim 12, wherein the dry powder contains only said active compounds.

14. The dry powder inhaler device of claim 12, wherein the dry powder contains, in addition to said active compounds, a pharmaceutically acceptable carrier.

15. The dry powder inhaler device of claim 12, wherein said substance is a sodium, potassium, or lysine salt of caprylic acid.

16. The dry powder inhaler device of claim 12, wherein said substance is a phospholipid.

17. The dry powder inhaler device of claim 12, wherein said substance is lysophosphatidylcholine.

18. The dry powder inhaler device of claim 12, wherein said substance is an alkyl glycoside.

19. The dry powder inhaler device of claim 12, in which at least 50% of the dry powder consists of (a) particles having a diameter of between 1 and 6 microns or (b) agglomerates of such particles.

20. The dry powder inhaler device of claim 12, wherein the ratio of (A) to (B) in said preparation is in the range of 9:1 to 1:1.

21. A dry powder inhaler device containing a therapeutic preparation comprising active compounds (A) insulin and (B) a substance which enhances the absorption of insulin in the lower respiratory tract, in the form of a dry powder suitable for inhalation in which at least 50% of the total mass of active compounds consists of (a) particles having a diameter of up to 10 microns or (b) agglomerates of such particles, provided that said substance is selected from the group consisting of an acyl carnitine and a salt of glycyrrhizine.

22. The dry powder inhaler device of claim 21, wherein the therapeutic preparation contains only said active compounds.

23. The dry powder inhaler device of claim 21, wherein the dry powder contains, in addition to said active compounds, a pharmaceutically acceptable carrier.

24. The dry powder inhaler device of claim 21, wherein said substance is a sodium or potassium salt of glycyrrhizine acid.

25. The dry powder inhaler device of claim 21, wherein said substance is decanoyl camitine, lauroyl carnitine, myristoyl camitine, or palmitoyl carnitine.

26. The dry powder inhaler device of claim 21, in which at least 50% of the dry powder consists of (a) particles having a diameter of between 1 and 6 microns or (b) agglomerates of such particles.

27. The dry powder inhaler device of claim 21, wherein the ratio of (A) to (B) in said preparation is in the range of 9:1 to 1:1.

28. A dry powder inhaler device comprising active compounds (A) insulin and (B) a substance which enhances the absorption of insulin in the lower respiratory tract, in the form of a dry powder suitable for inhalation in which at least 50% of the total mass of active compounds consists of (a) particles having a diameter of up to 10 microns or (b) agglomerates of such particles, provided that said substance is selected from the group consisting of an acyl carnitine and a salt of glycyrrhizine.

29. The dry powder inhaler device of claim 28, wherein the dry powder contains only said active compounds.

30. The dry powder inhaler device of claim 28, wherein the dry powder contains, in addition to said active compounds, a pharmaceutically acceptable carrier.

31. The dry powder inhaler device of claim 28, wherein said substance is a sodium or potassium salt of glycyrrhizine acid.

32. The dry powder inhaler device of claim 28, wherein said substance is an acyl carnitine.

33. The dry powder inhaler device of claim 28, in which at least 50% of the dry powder consists of (a) particles having a diameter of between 1 and 6 microns or (b) agglomerates of such particles.

34. The dry powder inhaler device of claim 28, wherein the ratio of (A) to (B) in said preparation is in the range of 9:1 to 1:1.

* * * * *

UNITED STATES PATENT AND TRADEMARK OFFICE
CERTIFICATE OF CORRECTION

PATENT NO. : 6,610,653 B1
DATED : August 26, 2003
INVENTOR(S) : Kjell G. E. Bäckström et al.

It is certified that error appears in the above-identified patent and that said Letters Patent is hereby corrected as shown below:

Column 7,
Lines 12-17, delete "Other potentially useful surfactants are sodium salicylate, sodium 5-methoxysalicylate, and the naturally occurring surfactants such as salts (e.g., sodium or potassium salts) of glycyrrhizine acid, saponin glycosides, and acyl camitines such as decanoyl camitine, lauroyl carnitine, myristoyl carnitine, and palmitoyl camitine." and insert -- Other potentially useful surfactants are sodium salicylate, sodium 5-methoxysalicylate, and the naturally occurring surfactants such as salts (e.g., sodium or potassium salts) of glycyrrhizine acid, saponin glycosides, and acyl carnitines such as decanoyl carnitine, lauroyl carnitine, myristoyl carnitine, and palmitoyl carnitine. --

Column 16,
Lines 23-24, delete "25. The dry powder inhaler device of claim 21, wherein said substance is decanoyl camitine, lauroyl carnitine, myristoyl camitine, or palmitoyl carnitine." and insert -- 25. The dry powder inhaler device of claim 21, wherein said substance is decanoyl carnitine, lauroyl carnitine, myristoyl carnitine, or palmitoyl carnitine. --

Signed and Sealed this

Fifteenth Day of June, 2004

JON W. DUDAS
*Acting Director of the United States Patent and Trademark Office*